US00PP29696P2

(12) United States Plant Patent
de Ruyver

(10) Patent No.: US PP29,696 P2
(45) Date of Patent: Sep. 18, 2018

(54) ***LAVANDULA* PLANT NAMED 'RUYLAS1704'**

(50) Latin Name: ***Lavandula* hybrid**
Varietal Denomination: RUYLAS1704

(71) Applicant: Kurt de Ruyver, Oudenaarde (BE)

(72) Inventor: Kurt de Ruyver, Oudenaarde (BE)

( * ) Notice: Subject to any disclaimer, the term of this patent is extended or adjusted under 35 U.S.C. 154(b) by 0 days.

(21) Appl. No.: 15/732,137

(22) Filed: Sep. 22, 2017

(51) Int. Cl.
*A01H 5/02* (2018.01)

(52) U.S. Cl.
USPC ..... Plt./445
CPC ..... *A01H 5/02* (2013.01)

(58) Field of Classification Search
USPC ..... Plt./445
CPC ..... A01H 5/02
See application file for complete search history.

*Primary Examiner* — Kent L Bell
(74) *Attorney, Agent, or Firm* — Samuel R. McCoy, Jr.

(57) ABSTRACT

'RUYLAS1704' is a new and distinctive variety of *Lavandula* plant which is characterized by a relatively compact growth habit, strong and thick greyed-green foliage with dense tomentose pubescence, strong stems and branches, an abundance of dark violet flowers borne on terminal spike inflorescences, and very large sterile bracts at the apex of each inflorescence. The new variety propagates successfully by stem cuttings and has shown to be uniform and stable in the resulting generations from asexual propagation.

3 Drawing Sheets

Latin name of the genus and species: The Latin name of the genus and species of the novel variety disclosed herein is *Lavandula* hybrid.

Variety denomination: The inventive variety of *Lavandula* disclosed herein has been given the variety denomination 'RUYLAS1704'.

BACKGROUND OF THE INVENTION

Parentage: 'RUYLAS1704' is the result of a controlled cross-pollination breeding program carried out by the inventor at a commercial nursery in Oudenaarde, Belgium, in June of 2015. The inventor performed a controlled cross-pollination of the seed parent, *Lavandula pedunculata* 'LOW2010-05' (U.S. Plant Pat. No. 27,157), and *Lavandula stoechas* 'Papillon' (not patented), the pollen parent. Seed from said cross was harvested, then germinated, and the resulting 1000 seedlings were grown to a mature size in order to evaluate for desirable commercial characteristics. In June of 2016, the inventor selected the new *Lavandula* cultivar due to its compact growth habit and large flowers. This new and distinctive cultivar was given the name 'RUYLAS1704'.

Asexual Reproduction: Asexual reproduction of 'RUYLAS1704' was first accomplished in August of 2016 by rooting softwood stem cuttings at a commercial greenhouse in Heythuysen, The Netherlands. Two successive generations have shown that the unique features of the instant cultivar are stable and reproduce true to type.

SUMMARY OF THE INVENTION

The cultivar 'RUYLAS1704' has not been observed under all possible environmental conditions and the phenotype may vary somewhat with variations in the instant environment such as temperature, day length, and light intensity, without, however, any variance in genotype. The following traits have been repeatedly observed and represent the distinguishing characteristics of the new *Lavandula* cultivar, 'RUYLAS1704'.

1. *Lavandula* 'RUYLAS1704' exhibits a relatively compact growth habit; and
2. *Lavandula* 'RUYLAS1704' exhibits strong and thick greyed-green foliage with dense tomentose pubescence; and
3. *Lavandula* 'RUYLAS1704' exhibits strong stems and branches; and
4. *Lavandula* 'RUYLAS1704' exhibits an abundance of dark violet flowers borne on terminal spike inflorescences; and
5. *Lavandula* 'RUYLAS1704' exhibits very large sterile bracts at the apex of each inflorescence.

BOTANICAL DESCRIPTION OF THE PLANT

Figure 1:
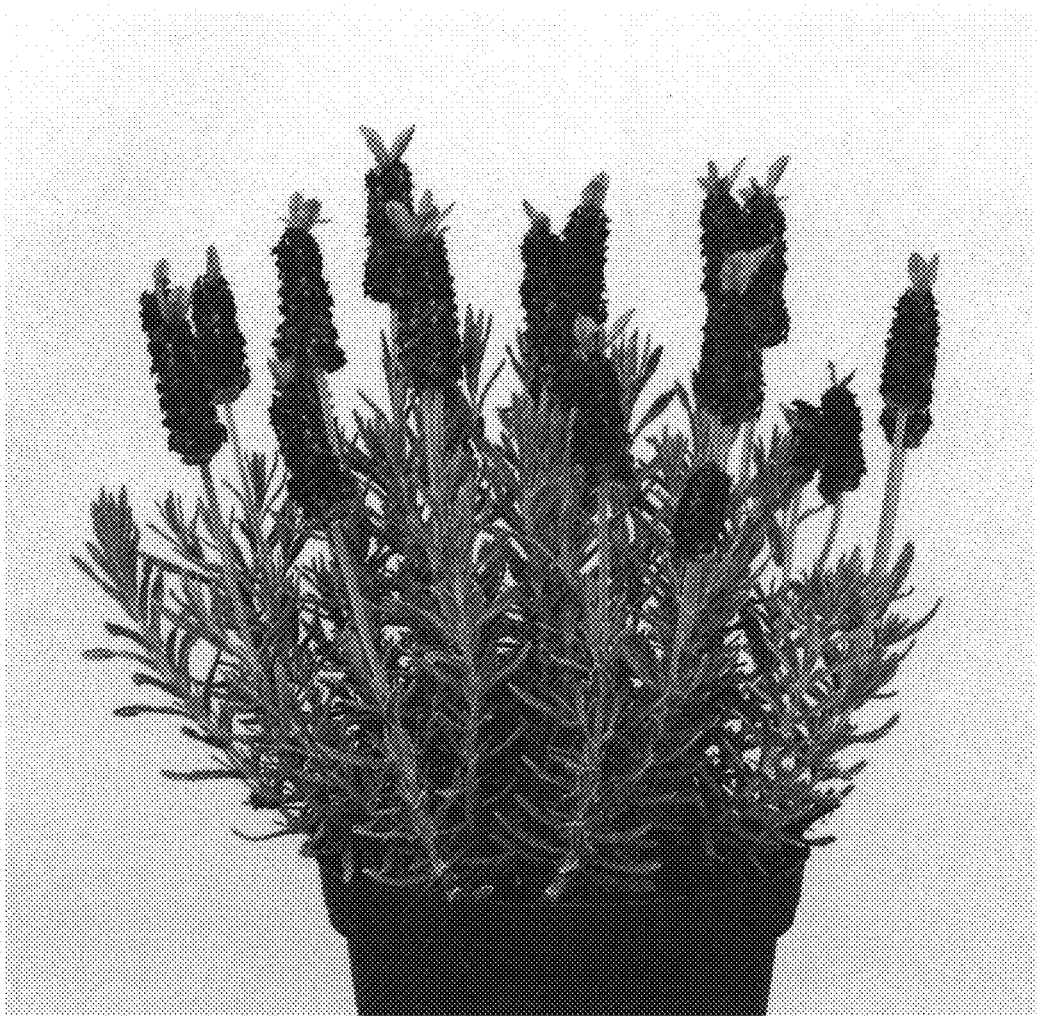
FIG. 1 shows, as nearly true as it is reasonably possible to make the same in color illustrations of this type, an exemplary 'RUYLAS1704' plant at approximately 30 months old, potted into a 13 cm nursery pot, grown outdoors in Oudenaarde, Belgium.
Figure 2:
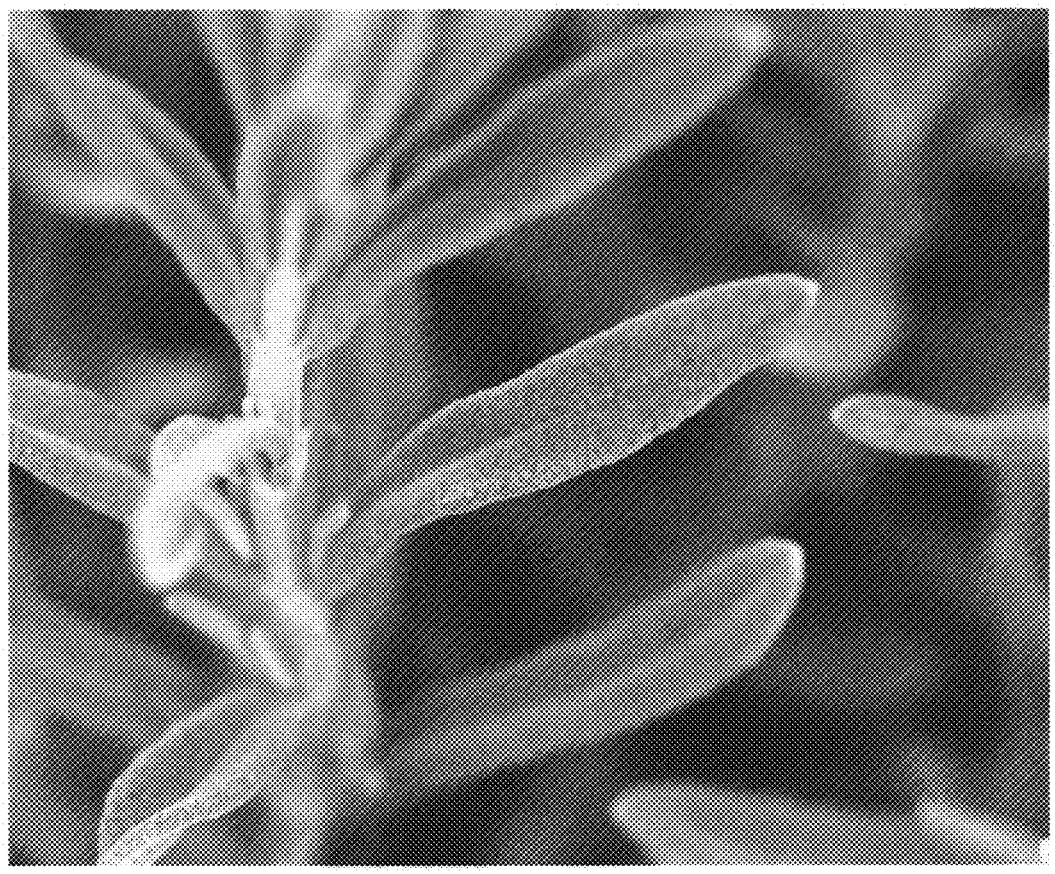
FIG. 2 shows, as nearly true as it is reasonably possible to make the same in color illustrations of this type, the typical foliage of the plant in FIG. 1.
Figure 3:
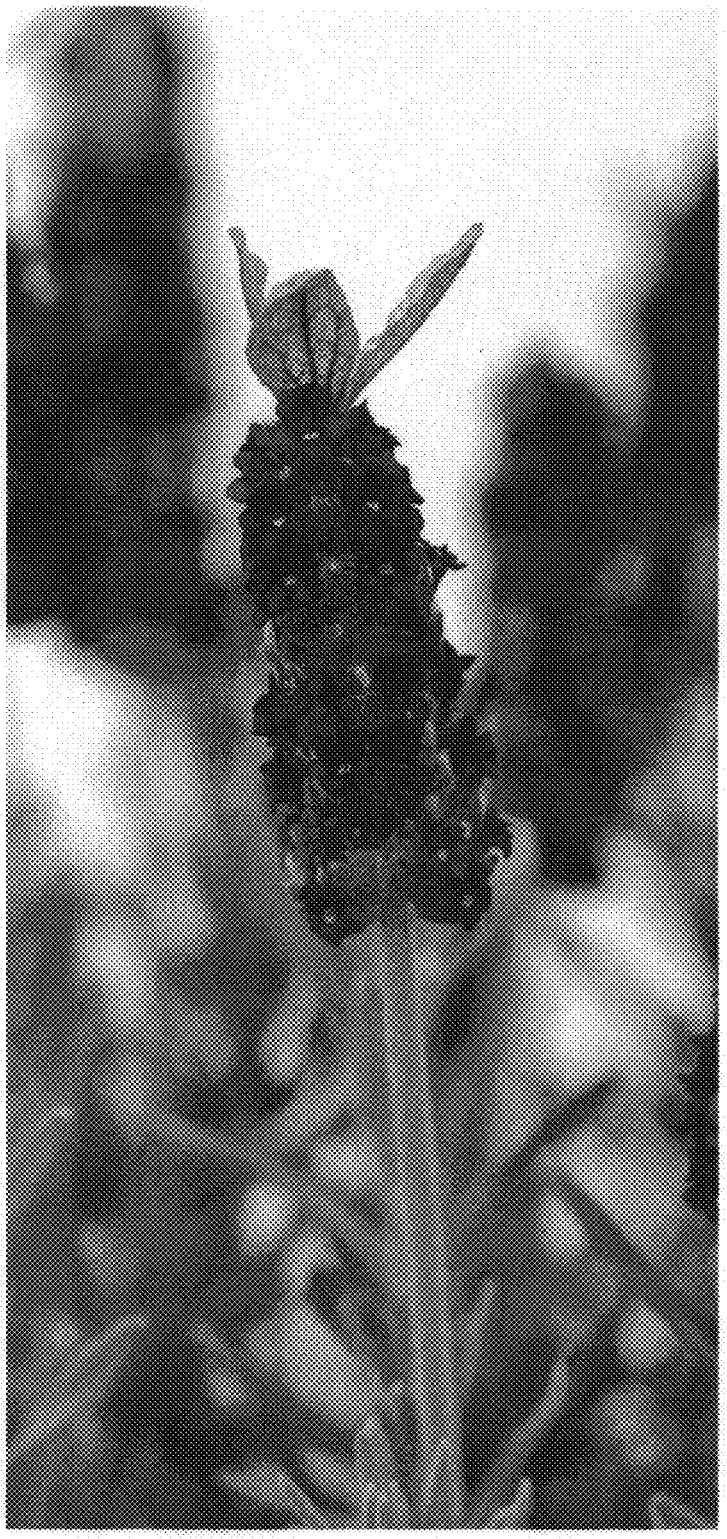
FIG. 3 shows, as nearly true as it is reasonably possible to make the same in color illustrations of this type, the typical inflorescence of the plant in FIG. 1.

The following is a detailed botanical description of a new and distinct variety of *Lavandula* known as 'RUYLAS1704', based upon observations of 30 month old field-grown plants in 13 cm nursery containers, produced in Oudenaarde, Belgium. Plants were grown using conventional production protocols for *Lavandula* plants which consisted of regular overhead irrigation and fertigation applications as needed. No pest or disease control measures were utilized in production. Plants were produced with full sun exposure and no photoperiodic treatments or artificial light was given to the plants. Observation data was recorded in August of 2017.

Those skilled in the art will appreciate that certain characteristics will vary with older or, conversely, with younger plants. 'RUYLAS1704' has not been observed under all possible environmental conditions. Where dimensions, sizes, colors and other characteristics are given, it is to be understood that such measurements are approximations or averages set forth as accurately as practicable. The phenotype of the variety may differ from the descriptions set forth herein with variations in environmental, climactic and cultural conditions. Color notations are based on *The Royal Horticultural Society Colour Chart*, The Royal Horticultural Society, London, 2015 edition.

A botanical description of 'RUYLAS1704' and comparisons with the parent plants are provided below.

General plant description:

*Growth habit*.—A broad, spreading to upright perennial subshrub.

*Plant form*.—Broad oblong to broad obovate.

*Height*.—15.6 cm to the top of the foliar plane; 19.7 cm to the top of the floral plane.

*Spread*.—23.6 cm.

*Plant vigor*.—Low to moderate.

*Growth rate*.—Low to moderate.

*Propagation*.—Softwood stem cuttings; rooting is initiated in approximately 14 days when grown in a greenhouse with an ambient average temperature of 18 degrees Celsius.

*Time to produce a finished plant*.—Approximately 12 weeks are required to produce a marketable finished plant in a 13 cm pot.

*Pest resistance and susceptibility*.—Not any more or less tolerant or susceptible to pests or diseases known to effect *Lavandula*.

*Environmental tolerances*.—Adapt to, at least, USDA Zones 7 to 10 and temperatures to at least 40 degrees Celsius; moderate tolerance to rain; high tolerance to wind.

Root system: Dense fibrous root system; relatively shallow; color of juvenile roots is nearest to yellow-white, RHS 158B; older roots are greyed-orange, RHS 163C.

Stem:

*Branching habit*.—Basally branching main stems; freely branching with lateral branches. Stems and branches are strongly aromatic, typical of *Lavandula stoechas*. Pinching isn't required but will improve branching.

*Number of primary (main) stems per plant*.—5.

*Number of secondary (lateral) branches per plant*.—32.

*Lateral branch length*.—10.6 cm.

*Lateral branch diameter*.—0.2 cm.

*Lateral branch internode length*.—0.8 cm.

*Appearance and shape*.—Quadrangular.

*Aspect of main stems*.—60 degrees from vertical, on average; varying between 0 and 70 degrees.

*Aspect of lateral branches*.—30 degrees to main stems.

*Luster*.—Matte, due to the dense woolly pubescence.

*Strength*.—Moderately strong.

*Color, juvenile*.—Yellow-green, nearest RHS 144B.

*Color, mature*.—Yellow-green, nearest to in between RHS 144A and N144A.

*Color of oldest stems*.—Brown, nearest to RHS N200B.

*Color at internodes*.—Yellow-green, nearest to in between RHS 144A and N144A.

*Pubescence*.—Tomentose; average length of hairs is 0.03 cm and colored green-white, nearest to RHS 157D.

Foliage:

*Arrangement*.—Opposite.

*Attachment*.—Sessile.

*Division*.—Simple.

*Attitude*.—Upward; apex occasionally curled upward or downward.

*Quantity*.—Average of 28 leaves per lateral branch.

*Fragrance*.—Strongly aromatic, typical of *Lavandula stoechas*.

*Lamina*.—Dimensions — 2.5 cm long and 0.4 cm wide, on average. Shape — Narrow oblanceolate. Aspect — Flat to very slightly twisted; slightly to moderately revolute. Apex — Acute. Base — Cuneate. Margin — Entire; slightly undulated. Pubescence of adaxial surface — Tomentose; average length of hairs is 0.02 cm and colored green-white, nearest to RHS 157D but lighter. Pubescence of abaxial surface — Tomentose; average length of hairs is 0.02 cm and colored green-white, nearest to RHS 157D but lighter. Luster of adaxial surface — Matte. Luster of abaxial surface — Matte. Color — Juvenile foliage, adaxial surface — Green, nearest to RHS 137B. Juvenile foliage, abaxial surface — Green, nearest to RHS 138B. Mature foliage, adaxial surface — Greyed-green, nearest to RHS 189A. Mature foliage, abaxial surface — Greyed-green, nearest to RHS 191A. Venation — Pattern — Pinnate. Venation color, adaxial surface — Green, nearest to RHS 138C. Venation color, abaxial surface — Green, nearest to RHS 138B.

Inflorescence:

*Type*.—Terminal spike.

*Natural flowering season*.—Late spring through late summer in Oudenaarde, Belgium.

*Time to flower*.—Approximately 13 weeks.

*Dimensions*.—4.8 cm high, not including peduncle, and 1.5 cm in diameter; the sterile bracts at the apex of each inflorescence have an average spread of 1.9 cm.

*Abundance of inflorescence*.—Very abundant.

*Quantity of open flowers and buds per inflorescence*.—140 flowers.

*Quantity of open flowers per plant*.—Approximately 900.

*Quantity of buds per plants*.—Approximately 3,200.

*Attitude*.—Upright.

*Peduncles*.—Length — Average of 5.2 cm. Diameter — Average of 0.175 cm. Attitude — Upright; 0 degrees to the lateral branches. Strength — Strong. Texture — Tomentose; average length of hairs is 0.03 cm and colored green-white, nearest to RHS 157D. Luster — Matte. Color — Green, RHS NN137D; yellow-green, nearest to 151B.

Flower buds:

*Shape*.—Oblong.

*Length*.—Average of 0.45 cm.

*Diameter*.—Average of 0.15 cm.

*Texture*.—Tomentose; average length of hairs is 0.03 cm and colored white, nearest to RHS NN155D.

*Luster*.—Matte.

*Color*.—Yellow-green, nearest to RHS 146C, and fading lighter towards the base, nearest to RHS 145C; apex where immature petals are exposed is violet, nearest to RHS 86A.

Flower:

*Flowering habit*.—Moderately freely flowering.

*Form*.—Salverform; petals fused into one upper lip which is split into two identical petal lobes, and one lower lip which is split into three identical petal lobes.

*Flower vertical height*.—0.4 cm.

*Flower diameter*.—0.4 cm.

*Flower length*.—0.7 cm.

*Floral throat diameter*.—0.15 cm.

*Floral throat texture*.—Glabrous; smooth.

*Diameter of floral tube*.—0.1 cm.

*Length of floral tube*.—0.45 cm.

*Floral tube texture, outer and inner surfaces*.—Distal one-third portion is moderately covered with a very short pubescence with an average length of 0.2 cm and colored violet, nearest to RHS N88D; the proximal two-thirds portion is glabrous and smooth.

*Aspect*.—Flowers are outward facing.

*Fragrance*.—Non-fragrant.

*Lastingness*.—Approximately 4 weeks.

*Persistent*.—Self-cleaning.

*Pedicels*.—Dimensions — 0.175 cm long and 0.075 cm in diameter. Aspect — Upward; approximately 50 degrees to the peduncle axis. Strength — Moderately strong. Texture — Moderately woolly pubescent; average length of hairs is 0.02 cm and colored green-white; hairs are so minute that it is impossible to accurately assign an R.H.S. color designation. Luster — Matte. Color — Yellow-green, RHS 147A.

*Petals*.—Quantity of Petals — 2. Arrangement — Labiate; one upper lip and one lower lip; proximal 75% of the petals are fused. Shape of petal lobes — Upper and lower petal lobes are spatulate. Dimensions, free portion of the upper petal — 0.7 cm long and 0.15 cm wide. Dimensions, free portion of the lower petal — 0.7 cm long and 0.15 cm wide. Apex — Both the upper and lower petal lobes are obtuse. Base — Fused into a tube. Margin — All petal lobes with entire margins which are moderately undulated. Aspect — Slightly curled upward at the apex of the lobes. Texture and luster of upper surface — Velvety; matte. Texture and luster of lower surface — Moderately velvety; slightly glossy. Petal color when opening, upper surface — Violet, nearest to RHS N87A. Petal color when opening, lower surface — Violet, nearest to RHS N87A. Petal color when fully opened, upper surface — Violet, nearest to RHS 83A yet slightly darker; color does not fade. Petal color when fully opened, lower surface — Violet, nearest to RHS 83A yet slightly darker; color does not fade. Petal venation — No venation is visible. Floral throat color — Violet, nearest to RHS 83C. Floral throat venation color — No venation is visible. Corolla tube color, when fully opened — Violet, RHS 83B, and fading white towards the base, RHS NN155D. Floral tube venation color — No venation is visible.

*Calyx*.—Shape — Campanulate. Length — 0.5 cm. Diameter — 0.15 cm. Sepals — Length — 0.5 cm. Width — 0.075 cm, but folded so appears narrower. Arrangement — Fused into a campanulate shape. Quantity — 5. Shape — Linear; fused into a campanulate shape. Apex — Obtuse. Base — Fused; only the distal 10 percent is free. Sepal lobe margin — Entire; not undulated. Texture and luster, upper surface — Glabrous, smooth; matte. Texture and luster, lower surface — Tomentose; average length of hairs is 0.02 cm and colored white, nearest to RHS NN155D; matte. Color when opening, upper surface — Yellow-green, nearest to RHS 146C, and fading lighter towards the base, nearest to RHS 145C. Color when opening, lower surface — Yellow-green, nearest to RHS 146C, and fading lighter towards the base, nearest to RHS 145C. Color when fully opened, upper surface — Yellow-green, nearest to a combination of RHS 146C and 146D, and fading lighter towards the base, nearest to RHS 145C. Color when fully opened, lower surface — Yellow-green, nearest to a combination of RHS 146C and 146D, and fading lighter towards the base, nearest to RHS 145C.

*Bract*.—Quantity — One fertile bract present at the base of each group of 5 individual flowers; 5 sterile bracts at the apex of each inflorescence. Fertile bract — Shape — Broad rhomboidal. Dimensions — Average of 0.6 cm long and 0.9 cm wide. Apex — Aristate. Base — Cuneate. Margins — Entire; not undulated. Texture and luster, upper surface — Glabrous; matte. Texture and luster, lower surface — Tomentose; average length of hairs is 0.02 cm and colored white, nearest to RHS NN155D; matte. Color, upper surface — Translucent purple, nearest to RHS 76C. Color, lower surface — Translucent purple, nearest to a combination RHS 76C and76D. Venation color, upper surface — Green, nearest to RHS 143A. Venation color, lower surface — Yellow-green, nearest to RHS 146B. Sterile bracts — Shape — Obovate to narrow obovate. Dimensions — Average of 1.5 cm long and 0.5 cm wide. Apex — Obtuse to bluntly acute. Base — Narrow cuneate. Margins — Entire; slightly undulated. Texture and luster, upper surface — Glabrous; rugose; matte. Texture and luster, lower surface — Glabrous and rugose except for the main vein which is lightly tomentose; average length of hairs is 0.02 cm and colored white, nearest to RHS NN155D; matte. Color, upper surface — Purple-violet, nearest to RHS N82B. Color, lower surface — Purple-violet, nearest to in between RHS N81B and N82B. Venation color, upper surface — Main vein is violet, nearest to RHS 83A. Venation color, lower surface — Main vein is purple, nearest to RHS N77A.

Reproductive organs:

*Stamens*.—Quantity — 4. Anthers — Attachment — Dorsifixed. Shape — Short kidney-shaped. Dimensions — Approximately 0.075 cm long and 0.01 cm wide. Color — Greyed-orange, nearest to RHS N164B. Filaments — Length — 0.075 cm, on average. Color — Purple-violet, nearest to RHS N82D.

Pollen, amount — Moderately abundant. Pollen color — Yellow-orange, nearest to RHS 15A.

*Pistil.*—Quantity — 1. Length — 0.35 cm. Style — Length — 0.3 cm. Color — Greyed-white, nearest to RHS 156D. Stigma — Shape — Club-shaped. Length — 0.05 cm. Diameter — 0.05 cm. Color — Greyed-purple, nearest to RHS N186A. Ovary Color — Yellow-green, nearest to RHS 146C.

Seed and fruit: No fruit or seeds have been produced to date.

COMPARISONS WITH THE PARENT PLANTS

Plants of the new cultivar 'RUYLAS1704' differ from its seed parent and closest known commercial comparator, *Lavandula pedunculata* 'LOW2010-05' (U.S. Plant Pat. No. 27,157), by the characteristics described in Chart 1.

Comparison Between 'RUYLAS1704' and 'LOW2010-05'

CHART 1

| Characteristic | 'RUYLAS1704' | 'LOW2010-05' |
|---|---|---|
| Length of lateral branches. | Shorter than 'LOW2010-05'. | Longer than 'RUYLAS1704'. |
| Rate of growth. | Slower rate of growth; no plant growth regulators required during production. | Fast growth; plant growth regulators required during production. |
| Flower size. | Flowers are longer. | Flowers are shorter. |

Plants of the new cultivar 'RUYLAS1704' differ from its pollen parent, *Lavandula stoechas* 'Papillon' (not patented), by the characteristics described in Chart 2.

Comparison Between 'RUYLAS1704' and 'Papillon'

CHART 2

| Characteristic | 'RUYLAS1704' | 'Papillon' |
|---|---|---|
| Winter hardiness. | Not winter hardy. | Winter hardy. |
| Flower size. | Smaller than 'Papillon'. | Larger than 'RUYLAS1704'. |

COMPARISONS WITH THE MOST SIMILAR VARIETY OF COMMON KNOWLEDGE

Plants of the new cultivar 'RUYLAS1704' differ from its closest known commercial comparator, *Lavandula pedunculata* 'IBPRU41016' (Community Plant Variety Rights application number 2017/0621), by the characteristics described in Chart 3.

Comparison Between 'RUYLAS1704' and 'IBPRU41016'

CHART 3

| Characteristic | 'RUYLAS1704' | 'IBPRU41016' |
|---|---|---|
| General coloration of the mature foliage. | Greyed-green. | Yellow-green. |
| Foliage attitude. | Upward. | Outward. |
| General coloration of open flowers. | Dark violet. | Light violet. |

That which is claimed is:

1. A new and distinct variety of *Lavandula* plant named 'RUYLAS1704', substantially as described and illustrated herein.

* * * * *